United States Patent
Mahadik et al.

(10) Patent No.: US 6,534,303 B2
(45) Date of Patent: Mar. 18, 2003

(54) PROCESS FOR THE PREPARATION OF ACIDIC LIPASE

(75) Inventors: Nutan Dattatraya Mahadik, Pune (IN); Digambar Vitthal Gokhale, Pune (IN); Kulbhushan Balwant Bastawde, Pune (IN); Jayant Malhar Khire, Pune (IN); Ulka Shrirang Puntambekar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/804,989

(22) Filed: Mar. 13, 2001

(65) Prior Publication Data

US 2002/0142399 A1 Oct. 3, 2002

(51) Int. Cl.$^7$ .............................. C12N 9/20; C12N 1/14; A01N 63/00
(52) U.S. Cl. .................... 435/198; 435/254.3; 435/917; 424/93.5; 424/94.6
(58) Field of Search .............................. 435/198, 254.3, 435/917; 424/94.6, 93.5

(56) References Cited

FOREIGN PATENT DOCUMENTS

DE      78201      *   7/1969

OTHER PUBLICATIONS

NCIM Catalogue of Fungi, 2002, pp. 69–84.*
Hawley's Condensed Chemical Dictionary, Edited by Lewis, 1997, 13th Edition, pp. 225, 350 and 351.*
Manual of Industrial Microbiology and Biotechnology, Edited by Demain et al., 1986, p. 103.*

* cited by examiner

Primary Examiner—Michael V. Meller
(74) Attorney, Agent, or Firm—Ladas & Parry

(57) ABSTRACT

The present invention provides a process for the preparation of acidic lipase from microbial sources with activity at highly acidic pH, the process comprising growing *Aspergillus niger* sp. in a fermentation medium containing carbon and nitrogen sources along with nutrients, separating the fungal biomass and recovering the culture filtrate/broth and separating the lipase enzyme.

4 Claims, No Drawings

PROCESS FOR THE PREPARATION OF ACIDIC LIPASE

FIELD OF THE INVENTION

The present invention relates to a process for the preparation of an acidic lipase. More particularly, the present invention relates to the production of thermostable and acid stable lipase using *Aspergillus niger*.

BACKGROUND OF THE INVENTION

Research on microbial lipases has increased in recent years because of their practical application in industry in the hydrolysis of fats, production of fatty acids and food additives, synthesis of esters and peptides, resolution of racemic mixtures or as additives for detergents. [Bjorkling F., Godtfredsen S. E., and Kirk O., (1991), Trends Biotechnol. 9, 360–363]. These enzymes are widely distributed in filamentous fungi [Sugihara A., Shimada Y., and Tominaga Y., (1990), J. Biochem. 107, 426–430; Torossian K. and Bell A. W. (1991) Biotechnol. Appl. Biochem. 13, 205–211; Yadav R. P., Saxena R. K., Gupta R., and Davidson W. S., (1998) Biotechnol. Appl. Biochem. 28, 243–249], yeasts [Kalkote U. R., Joshi R. A., Ravindranathan T., Bastawade K. B., Patil S. G., and Gokhale D. V., (1992) Biotechnol. Lett. 14, 785–788; Valero F., Ayats F., Lopez-Santin J., and Poch M. (1998) Biotechnol. Lett. 10, 741–744; Dalmau E., Montesions J. L., Lotti M. and Casas C., (2000), Enzyme Microb. Technol. 26, 657–663] and bacteria [Jaeger K. E., Ransae S., Dijkstra B. W., Colson C., van Heuvel M. S. and Misset O. (1994) FEMS Microbiol. Rev. 15, 29–63; Jaeger K. E., Dijkstra B. W. and Reetz M. T., (1999) Ann. Rev. Microbiol. 53, 315–351].

Filamentous fungi are preferred sources of lipase since they secrete the enzymes extracellularly. The most productive strains known till date belong to the genera Rhizopus, Mucor, Geotrichum, Penicillium and Aspergillus [Bjorkling F., Godtfredsen S. E., and Kirk O., (1991), Trends Biotechnol. 9, 360–363]. An acid resistant lipase preparation active between pH 4.5–5.5 was reported from *Aspergillus niger* [Torossian K. and Bell A. W. (1991) Biotechnol. Appl. Biochem. 13, 205–211]. Lipases active at highly acidic pH's have not been reported so far from microbial sources. Such acidic lipases have potential applications in the food industry. It is therefore desirable to obtain such acidic lipases which are active at highly acidic pH from microbial sources.

OBJECTS OF THE INVENTION

The main object of the invention is to provide a process for the preparation of acidic lipase which is active even at highly acidic pH from microbial sources.

It is another object of the invention to provide a process for the preparation of acidic lipase which is active even at highly acidic pH using *Aspergillis niger*.

SUMMARY OF THE INVENTION

Accordingly the present invention provides a process for the preparation of acidic lipase, said process comprising growing *Aspergillus niger* sp. in a conventional fermentation medium containing carbon and nitrogen sources along with conventional nutrients for a period in the range of 72–96 hours at a temperature in the range of 25° C. to 35° C. under agitation, separating the fungal biomass and recovering the culture filtrate/broth and separating the lipase enzyme.

In one embodiment of the invention, the fungal strain used is isolated from decaying wood and is deposited at the National Collection of Industrial Microorganisms (NCIM), Biochemical Sciences Division, National Chemical Laboratory, Pune 411 008, India and designated as *Aspergillus niger* NCIM 1207.

In another embodiment of the invention, the dry mycelium of *Aspergillus niger* is prepared after harvesting the growth of the fungal strain, washing the mycelium with distilled water followed by washing with chilled acetone, drying the acetone treated mycelium under vacuum for 6–10 hours to remove acetone and water.

In a further embodiment of the invention, a CELITE (diatomaceous earth) bound (extracellular) enzyme is prepared by adding CELITE (diatomaceous earth) 545 (1 gm) to culture filtrate (20 ml) with mixing, ice cold acetone (25 ml) added to the suspension over a period of 5 minutes while stirring, the resultant suspension stirred for another 30 minutes using a magnetic stirrer at 0° C., filtered and dried.

DETAILED DESCRIPTION OF THE INVENTION

The dry mycelium of *Aspergillus niger* is prepared after harvesting the growth of the fungal strain, washing the mycelium with distilled water followed by washing with chilled acetone, drying the acetone treated mycelium under vacuum for 6–10 hours to remove acetone and water. The vacuum dried mycelial preparation was used for the estimation of cell bound (intracellular) activity on the basis of formation of esters.

CELITE (diatomaceous earth) bound (extracellular) enzyme is prepared by adding CELITE (diatomaceous earth) 545 (1 gm) to culture filtrate (20 ml) with mixing. Ice cold acetone (25 ml) was then added to the suspension over a period of 5 minutes while stirring, the resultant suspension stirred for another 30 minutes as source of extracellular enzyme. The extracellular enzyme activity was measured on the basis of formation of butyl esters.

*Aspergillus niger* NCIM 1207 was used. Fermentation was done under submerged conditions. Lipase enzyme was produced by growing *Aspergillus niger* strain on a conventional growth medium such as MGYP (malt extract 0.3%; glucose 5.0%; yeast extract 0.3%; peptone 0.5% and Agar 2.0%) for 8–10 days at 25–30° C. The fermentation medium used was selected from MGYP liquid medium and basal oil based (BOB) medium ($NaNO_3$ 0.05%; $MgSO_4.7H_2O$ 0.05%; KCl 0.05%; $KH_2PO_4$ 0.2%; yeast extract 0.1%; peptone 0.5%; and olive oil 2.0%). All the media were sterilised at 15 lbs for 20 minutes. The pH of the media was adjusted to 5.5 prior to sterilisation. Resultant fermentation medium was inoculated with spores ($10^8$–$10^9$) from fully grown agar slope and was incubated at 25–30° C. for 72–96 hours with shaking at 150–180 rpm. Biomass was separated by known methods such as filtration to recover the broth and lipase activity was estimated by pNPP assay or on the basis of formation of butyl esters (indicative of lipase activity).

The process of the invention is described further with reference to the following examples, which are merely illustrative and are not to be construed as limiting the scope of the invention.

EXAMPLE 1

Culture was grown in 500 ml conical flasks with 100 ml of fermentation medium. The medium was inoculated with spores ($10^8$ $10^9$) from 8 days old MGYP slope and incubated at 30° C. with shaking. The mycelium was harvested by filtration and the culture filtrate is used as the source of extracellular enzyme. Lipase activity is based on the formation of butyl esters by transesterification of butter oil with butanol. The transesterification reaction was carried out in a 25 ml stoppered conical flask, which was shaken at 100 strokes per minute in a controlled temperature water bath, normally at 37° C. for 24 hours. The reaction mixture contained 50 mg vacuum dry mycelium or 500 mg CELITE (diatomaceous earth) absorbed enzyme preparation, 250 mg butter oil and 5.5 gm water saturated butanol. Fifty microlitre of water/buffer was added to the reaction mixture when the vacuum dried mycelial preparation was used. Analysis of esters was carried out by GLC using capillary column (Phillips, 0.25 um film of silicon OV1, 3.8 m×90.22 mm; injector and FI detector at 300° C.). For samples that contain incompletely solvolyzed or unchanged triglycerides, the temperature was set at 40° C. for 3 minutes then rising at 3° C. per minute up to 320° C. to elute unchanged triglycerides. Esters were identified by interpolation from standards. Analysis was carried out on 1u1 samples using added undecane (0.15 mg ml$^{-1}$) as an internal standard which was prepared in n-hexane. For fast and routine measurements of lipase activity, the spectrophotometric method of p-nitrophenylpalmitate (pNPP) was used. The method was slightly modified as follows: solution A: 40 mg of pNPP dissolved in 12 ml of propan—2 ol; solution B: 0.1 g of gum Arabic and 0.4 g of Triton X—100 dissolved in 90 ml of water. The substrate solution was prepared by adding 1 ml of solution A to 19 ml of solution B dropwise and under intense stirring to get an emulsion which remained stable for at least 2 hours. For lipase activity measurement, the assay mixture consisting of 0.9 ml substrate solution, 0.1 ml buffer (0.5 M) and 0.1 ml of suitable diluted enzyme, was incubated for 20 minutes at suitable temperature (30–60° C.). The p-nitrophenol liberated was measured at 410 nm.

TABLE 1

| Medium | Biomass (mg dry weight)* | Ester formed (mg ml$^{-1}$) | |
|---|---|---|---|
| | | Intracellular | Extracellular |
| MGYP | 450 ± 23 | Not detected | Not detected |
| BOB | 1350 ± 95 | 0.58 | 2.25 |

*the biomass was obtained from 100 ml of fermentation medium.

All the values are the averages of three independent experiments and the standard deviation ranges between 5–8%.

Table 1 shows the growth and enzyme production in MGYP and BOB media. Data on the formation of one of the esters (butyl oleate) are presented since it is not practical to show all the different esters formed. *Aspergillus niger* NCIM 1207 produced neither intracellular nor extracellular activity in MGYP medium. Lipase production appeared to be inducible since both intra- and extracellular lipase activity was detected in only oil based medium, with maximum activity detected extracellularly.

EXAMPLE 2

The effect of temperature on enzyme activity was studied by incubating the assay mixture at temperatures ranging between 30° C. to 70° C. for 20 minutes. The assay mixture consisted of 0.9 ml of the substrate (pNPP), 0.1 ml of citrate buffer (pH 2.5, 0.5 M) and 0.1 ml of suitable diluted enzyme. The p-nitrophenol released was measured at 410 nm. It was observed that the enzyme was active over a broad temperature range between 35° C. to 60° C. with maximum activity at 45° C.

EXAMPLE 3

The effect of different pH's on lipase activity was studied using the buffer systems (0.05 M), KCl—HCl buffer (pH 1.5 and 2.0), citrate phosphate (pH 2.5–6.0). Assay mixture consisting of 0.9 ml substrate solution (pNPP), 0.1 ml buffer (0.5 M) and 0.1 ml of suitable diluted enzyme was incubated at 45° C. and p-nitrophenol released was measured at 410 nm. It was observed that enzyme was active at pH 2.5–3.0.

EXAMPLE 4

The temperature stability studies for lipase enzyme were carried out by incubating the extracellular enzyme (culture filtrate) at different temperatures between 30° C. to 70° C. and estimating the residual activity after different time intervals (1 hour to 4 hours). The residual enzyme activity was determined using pNPP substrate. Assay mixture consisting of 0.9 ml substrate solution (pNPP), 0.1 ml buffer (pH 2.5, 0.5 M) and 0.1 ml of suitably diluted enzyme was incubated at 45° C. and p-nitrophenol released was measured at 410 nm. The enzyme was found to be stable at temperatures between 30° C. and 60° C. for 4 hours.

EXAMPLE 5

The stability of the enzyme at different pH's (1.5–9.0) was studied by incubating the extracellular enzyme (culture filtrate) at 40° C. and at as different pH (KCl—HCl buffer, pH 1.5 and 2.0; Citrate phosphate, pH 2.5–7.0; boric acid—borax buffer, pH 8.0–9.0) and estimating the residual activity at different time intervals (1 hour to 4 hours) by pNPP assay. Assay mixture consisting of 0.9 ml substrate solution (pNPP), 0.1 ml buffer (pH 2.5, 0.5 M) and 0.1 ml of suitably diluted enzyme was incubated at 45° C. and p-nitrophenol released was measured at 410 nm. The enzyme was stable up to 4 hours between wide pH range (3.0–9.0) with slight decline in enzyme activity when incubated at pH 2.0.

We claim:

1. A process for the preparation of acidic lipase comprising the steps of:
   (a) growing *Aspergillus niger* NCIM 1207 in a fermentation medium containing a carbon source, a nitrogen source and nutrients for a period of 72–96 hours at a temperature in the range of 25° C. to 35° C. under agitation to obtain a fungal biomass;
   (b) separating the fungal biomass to obtain a culture filtrate; and
   (c) separating the acidic lipase from the culture filtrate.

2. A process for the preparation of extracellular acidic lipase comprising the steps of:
   (a) growing *Aspergillus niger* NCIM 1207 in a fermentation medium containing a carbon source, a nitrogen source and nutrients for a period of 72–96 hours at a temperature in the range of 25° C. to 35° C. under agitation to obtain a fungal biomass;
   (b) separating the fungal biomass to obtain a culture filtrate;
   (c) adding a diatomaceous earth to the culture filtrate; and
   (d) recovering extracellular acidic lipase from the culture filtrate of step (c).

3. A process as claimed in claim 2 wherein acetone is added in step c) to obtain a suspension.

4. A process as claimed in claim 2 wherein 1 gm of diatomaceous earth is added to 20 ml of the culture filtrate of step c) and mixed to obtain a suspension, 25 ml of ice cold acetone is then added to the suspension over a period of 5 minutes and stirred to obtain a resultant suspension, and the resultant suspension is subsequently stirred for 30 minutes using a magnetic stirrer at 0° C.

* * * * *